US009820850B2

(12) United States Patent
Mentak

(10) Patent No.: US 9,820,850 B2
(45) Date of Patent: Nov. 21, 2017

(54) POLYMERS AND METHODS FOR OPHTHALMIC APPLICATIONS

(75) Inventor: Khalid Mentak, San Ramon, CA (US)

(73) Assignee: KEY MEDICAL TECHNOLOGIES, INC., San Ramon, CA (US)

( * ) Notice: Subject to any disclaimer, the term of this patent is extended or adjusted under 35 U.S.C. 154(b) by 629 days.

(21) Appl. No.: 13/411,836

(22) Filed: Mar. 5, 2012

(65) Prior Publication Data

US 2013/0231740 A1    Sep. 5, 2013

(51) Int. Cl.
| | |
|---|---|
| *A61F 2/16* | (2006.01) |
| *A61L 27/16* | (2006.01) |
| *C08F 2/50* | (2006.01) |
| *C08F 220/20* | (2006.01) |
| *C08F 220/18* | (2006.01) |
| *C08F 226/12* | (2006.01) |
| *B29D 11/00* | (2006.01) |
| *G02B 1/04* | (2006.01) |

(52) U.S. Cl.
CPC .............. *A61F 2/1624* (2013.01); *A61F 2/16* (2013.01); *A61L 27/16* (2013.01); *B29D 11/00461* (2013.01); *C08F 2/50* (2013.01); *C08F 220/18* (2013.01); *C08F 220/20* (2013.01); *C08F 226/12* (2013.01); *A61L 2430/16* (2013.01); *G02B 1/041* (2013.01)

(58) Field of Classification Search
CPC ........ A61F 2/16; A61L 27/16; A61L 2430/16; C08F 2/50; C08F 226/12; C08F 220/18; C08F 220/20
USPC ......... 623/6.12, 6.13, 6.14, 6.15, 6.16, 6.17, 623/6.6, 6.59; 606/107
See application file for complete search history.

(56) References Cited

U.S. PATENT DOCUMENTS

| | | | | |
|---|---|---|---|---|
| 4,808,182 A | * | 2/1989 | Barrett | 623/6.6 |
| 5,147,394 A | * | 9/1992 | Siepser et al. | 623/6.6 |
| 5,480,950 A | | 1/1996 | Wang et al. | |
| 5,693,095 A | | 12/1997 | Freeman et al. | |
| 5,810,833 A | * | 9/1998 | Brady et al. | 606/107 |
| 7,399,811 B2 | | 7/2008 | Mentak et al. | |
| 7,446,157 B2 | | 11/2008 | Mentak et al. | |
| 7,745,555 B2 | | 6/2010 | Mentak et al. | |
| 7,842,367 B2 | | 11/2010 | Mentak | |
| 7,857,848 B2 | | 12/2010 | Mentak | |
| 7,988,701 B2 | | 8/2011 | Vaquero et al. | |
| 8,048,972 B2 | | 11/2011 | Mentak et al. | |
| 8,420,753 B2 | | 4/2013 | Mentak et al. | |
| 9,056,934 B2 | | 6/2015 | Mentak | |
| 2002/0049290 A1 | | 4/2002 | Vanderbilt | |
| 2005/0222578 A1 | | 10/2005 | Vaquero | |
| 2006/0252844 A1 | | 11/2006 | Mentak | |
| 2007/0010883 A1 | * | 1/2007 | Mentak | A61L 27/16 623/6.58 |
| 2007/0060925 A1 | | 3/2007 | Pynson | |
| 2007/0233240 A1 | * | 10/2007 | Frank et al. | 623/6.59 |
| 2008/0064821 A1 | * | 3/2008 | Mentak et al. | 525/333.3 |
| 2011/0071629 A1 | | 3/2011 | Mentak | |

FOREIGN PATENT DOCUMENTS

| | | |
|---|---|---|
| JP | 2011-246673 A | 12/2011 |
| WO | 2007/142782 A2 | 12/2007 |

OTHER PUBLICATIONS

International Preliminary Report on Patentability for international application No. PCT/US2013/027710, dated Sep. 9, 2014, 5 pages.

* cited by examiner

*Primary Examiner* — Katrina Stransky

(74) *Attorney, Agent, or Firm* — Husch Blackwell LLP

(57) ABSTRACT

The present invention relates to novel methods and materials particularly useful for ophthalmic applications and to methods for making and using the same. More particularly, the present invention relates to relatively soft, optically transparent, foldable, high refractive index materials particularly suited for use in the production of intraocular lenses, contact lenses, and other ocular implants and to methods for manufacturing and implanting IOLs made therefrom.

10 Claims, No Drawings

POLYMERS AND METHODS FOR OPHTHALMIC APPLICATIONS

FIELD OF INVENTION

The present invention relates to novel materials particularly useful for ophthalmic applications and methods for making and using the same. More particularly, the present invention relates to relatively soft, optically transparent, foldable, high refractive index materials particularly suited for use in the production of intraocular lenses, contact lenses, and other ocular implants and to methods for manufacturing and using the same.

BACKGROUND OF THE INVENTION

Since the 1940's optical devices in the form of intraocular lenses (IOLs) have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lenses was poly(methyl methacrylate) (PMMA), which is a rigid, glassy polymer.

Softer, more flexible IOLs have gained in popularity in recent years due to their ability to be compressed, folded, rolled or otherwise deformed. Such softer IOLs may be deformed prior to insertion thereof through an incision in the cornea of an eye. Following insertion of the IOL in an eye, the IOL returns to its original, pre-folded shape due to the memory characteristics of the soft material. Softer, more flexible IOLs as just described may be implanted into an eye through an incision that is less than 4.0 mm i.e., much smaller than the 5.5 to 8.0 mm incision necessary to implant more rigid IOLs such as those made from PMMA. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have occasionally been found to be associated with an increased incidence of postoperative complications, such as induced astigmatism.

With recent advances in small-incision cataract surgery, increased emphasis has been placed on developing soft, foldable polymer materials suitable for use in artificial IOLs. In general, these materials fall into one of three categories: hydrogels, silicones and low glass transition temperature acrylics.

A further recent advance in IOL implantation is the use of IOL injectors to implant the IOL in the eye. Cf., US 2007/0060925 "Preloaded IOLS Injector and Methods" to Pynson; US 2005/0222578 "IOL Injector" to Vaquero; and U.S. Pat. No. 7,988,701 "Preloaded IOL Injector" to Vaquero et al.; each of which are incorporated by reference herein in their entireties. Unfortunately injector implantation of an IOL generally proceeds more smoothly (i.e., with fewer surgical difficulties) the more rigid and thus generally the more handleable, the IOL.

Thus, for surgical purposes a more rigid lens is suggested. Usually this means a less than fully hydrated polymer lens is injected. As is well known, post-implantation hydration of an IOL changes, sometimes unpredictably, the refractive index (RI) of the lens. This subjects the physician and the injectable IOL implantation to uncertainty as to the surgical outcome. This invention in one aspect reduces or eliminates that uncertainty of surgical outcome in the context of a post-implantation hydratable or hydrating IOL polymer, particularly where implantation is accomplished using an IOL injector.

In general, high water content hydrogel materials have relatively low refractive indices, making them less desirable than other materials with respect to minimal incision size. Low refractive index materials require a thicker IOL optic portion to achieve a given refractive power. Silicone materials may have a higher refractive index than high-water content hydrogels, but tend to unfold too rapidly after being placed in the eye in a folded position. A too rapid unfolding of a folded lens can potentially damage the corneal endothelium and/or rupture the natural lens capsule and associated zonules. Low glass transition temperature acrylic materials are desirable because they typically have a high refractive index and unfold more slowly and more controllably than silicone materials when inserted into e.g., the lens capsule. Unfortunately, low glass transition temperature acrylic materials, which contain little or no water initially, may absorb pockets of water, in vivo, causing light reflections or "glistenings". Furthermore, it is difficult to achieve ideal folding and unfolding characteristics due to the temperature sensitivity of acrylic polymer memory.

U.S. Pat. No. 5,480,950 issued Jan. 2, 1996 teaches of high refractive index hydrogel materials having a hydrated equilibrium water content ("EWC") of at least 57% for use in the manufacture of IOLs. The high refractive index hydrogel materials are cross-linked polymers prepared from mixtures of N-vinylpyrrolidone, 4-vinylpyrimidine and a vinyl pyridine having equilibrium water contents up to 90% and refractive indexes of 1.560 to 1.594 in the dry state. The IOLs as described are not implanted in a hydrated state. Rather, the IOLs are implanted in a dry, folded and elongated state and hydrated in situ. The refractive indexes in the hydrated state as used in the eye are not provided. U.S. Patent Application Publication 2002/0049290 relates to high refractive index (RI) ophthalmic hydrogel materials U.S. Pat. No. 5,693,095 issued Dec. 2, 1997 teaches of high refractive index, low water content IOL materials. The materials taught in this particular patent are acrylic materials having an elongation of at least 150%. IOLs manufactured from a material having such elongation characteristics will not crack, tear or split when folded. However, such low water content acrylic materials have been found to be less biocompatible than other materials when manufactured into and used as IOL devices.

In the past decade, hydrophobic polymers have been used in IOL manufacturing with some success. The ophthalmic community has accepted this type of polymer as having good physical properties and acceptable biocompatibility in ocular environments. However, current IOLs made from conventional hydrophobic polymers sometimes suffer from poor optical stability in ocular fluids (e.g. glistenings, optical artifacts) and low refractive indices. The formation of unwanted particles and deposits in the bulk of hydrophobic polymers is attributed to uncontrolled water sorption and subsequent phase separation. Conventional homopolymers currently used to produce copolymers with high RIs (>1.51) absorb varying amounts of water in a sporadic fashion, creating phase separation, haze, and glistenings.

Currently, there are no foldable, high RI IOL polymers that resist the formation of glistenings and deposits. Compositions known to resist formation of glistenings require hydration prior to implantation. This limits foldability, incision size, and preloading packaging, which quickly becoming the method of choice for packaging IOLs. More importantly, there are no IOLs made with polymers with EWC having a value of in the range of about 3% to about 15% by weight. Not wishing to be bound by any theory, it is believed, however that this family of polymers is more resistive to glistenings. In this invention, compositions and method to manufacture glistening-free IOLs with EWC of 5-15% are provided.

SUMMARY OF THE INVENTION

The present invention is a new family of high RI polymers particularly suitable for, but not limited to, foldable IOL applications. Materials of this invention are optically stable in ocular fluids and resist the formation of unwanted optical artifacts. The unusual properties of the copolymers of this invention are achieved by incorporating a hydrophilic polymer within a very hydrophobic polymer matrix that allows the copolymer to have a specific EWC in the range of about 3% to about 15% by weight, preferably in the range of about 4% to about 10% by weight. In addition, the limited amount of water that is absorbed is well distributed and well dispersed within the matrix, preventing macrophase separation noted in prior art compositions. The result is an optically clear material with stable optical properties.

It is well understood that such compositions may result in IOLs with dioptric powers that changes upon implantation in the eye. Another aspect of this invention is to anticipate empirically the change in dioptic power via measurements of IOL diopter in a hydrated state prior to drying and sterilization for packaging. Thus, in this further aspect, the present invention is a method for determining the "after implantation" or post-implantation refractive index/diopter of an intraocular lens. In this method the lens, usually but not always an intraocular lens, after manufacture, is in a substantially dehydrated state so as to be sufficiently handleable to be implanted into the eye through an incision in the cornea e.g., by means of an IOL injector. That lens after manufacture is hydrated by e.g., soaking it in saline solution e.g., for 24 hours, at room temperature. The diopter of the hydrated lens is measured while the polymer of the lens is in a hydration state similar to the state of hydration it would or will obtain when it is implanted in the eye. The diopter of the IOL is then measured in its hydrated state outside of the eye. The lens then is at least partially dehydrated sufficiently to be sterilized and stored in a substantially dry state to where it is sufficiently handleable to be implanted by means of e.g., an IOL injector. The implanted IOL then is implanted in the eye using an injector through a corneal incision. The implanted, partially dehydrated IOL then hydrates within the eye to where it equilibrates to substantially the same refractive index (and thus diopter) obtained by measurement while it was hydrated prior to implantation. In this practice of the invention, post-implant hydrated IOL refractive index is obtained with approximately 100% certainty while simultaneously obtaining all the advantages of injector or injector-based IOL implantation processes.

In one aspect the present invention is a method of determining post-implantation diopter of a lens pre-implantation comprising the steps of:
   providing an intraocular lens OOP comprising a polymer for which the rigidity and refractive index is dependent upon its state of hydration;
   exposing the lens before implantation to a hydrating liquid for a sufficient length of time that the polymer of the IOL hydrates to a state of hydration which is substantially similar to the state of hydration the IOL polymer will obtain post-implantation;
   measuring the diopter value of the substantially hydrated lens;
   partially dehydrating the lens to enhance its handling characteristics;
   implanting the partially dehydrated IOL in an eye; and
   permitting the partially dehydrated lens to hydrate in the eye post-implantation to where it obtains the diopter value substantially that of the lens measured pre-implantation.

This invention relates to novel copolymers particularly adaptable to intraocular lenses ("IOL"), contact lens, and other ophthalmic and optical applications. IOLs made from the materials of this invention have a very high refractive index, and may be machined or molded at around room temperature. IOLs of this invention may be folded and used to replace a defective natural lens of the eye by insertion through a small incision without the need for further processing or hydration. A particular advantage of the materials of this invention is their unusual hybrid character that prevents uncontrolled water sorption.

Foldable ophthalmic lens materials having controllable, uniform, relatively high water content and unexpectedly high refractive indices particularly suited for use as intraocular lenses (IOLs), or other ophthalmic devices such as but not limited to contact lenses, keratoprostheses and corneal rings or inlays, are the primary loci of the present invention.

This invention relates to copolymer compositions comprising limited amounts of a monomer having an aromatic monomer and/or a carbazole and/or naphthyl moiety, carbazole, naphthalene, or a naphthyl group and/or a hydrophobic monomer. Carbazole and or naphthyl moiety monomers are added to the comonomer to increase the refractive index of the comonomer and increase the ability of the copolymer material to block blue light (wavelength up to 475 nm). A monomer having a surface tension generally in the range of 50 dyn/cm or less is used to create a very hydrophobic matrix. A hydrophilic polymer is added to create a hydrophilic phase (in a process described below) for controlled water sorption.

Accordingly, it is an object of the present invention to provide a biocompatible IOL material having a high refractive index.

Another object of the present invention is to provide an IOL material having a high refractive index- and controlled water sorption;

Still another object of the present invention is to provide a method to allow accurate targeting of the power of the lens in-vivo.

Still another object of the present invention is to provide an IOL material that is relatively simple to manufacture.

These and other objectives and advantages of the present invention, some of which are specifically described and others that are not, will become apparent from the detailed description and the claims that follow.

DETAILED DESCRIPTION OF THE INVENTION

Materials of the present invention with high refractive indexes are desirable to allow manufacturers to manufacture thinner IOLs. A thin IOL or thin IOL optic is critical in enabling a surgeon to minimize incision size. Keeping the surgical incision size to a minimum reduces intraoperative trauma and postoperative complications. A thin IOL is also critical for accommodating certain anatomical locations in the eye such as the anterior chamber and the ciliary sulcus. IOLs may be placed in the anterior chamber for increasing visual acuity in both aphakic and phakic eyes and placed in the ciliary sulcus for increasing visual acuity in phakic eyes.

The preferred materials of the present invention have the flexibility required to allow the same to be folded or deformed so that IOLs made therefrom may be introduced into an eye through the smallest possible incision.

The novel materials of the present invention are copolymers, trimers, tetramers, etc., comprising at least two monomeric components:

a hydrophobic monomer, and a hydrophilic monomer. A cross linker generally is included as is a UV absorber.

The compositions comprise multimers including: a first monomer containing an aromatic, carbazole and or naphthyl moiety, the aromatic/carbazole/naphthyl moiety monomer being present in the composition at a concentration of at least 25% and preferably up to about 35-80%.

The composition further includes a second monomer with a hydrophobic homopolymer, the hydrophobicity being defined as the homopolymer having a surface tension of about 50 dyn/cm or less, the second monomer being present in the copolymer in an amount of at least about 20 weight percent, preferably about 50-60 weight %.

The composition then includes at least about 10 weight % of a hydrophilic monomer, preferably about 20-30 weight %. The composition then includes a crosslinking monomer, the crosslinking monomer being present at a concentration in the range up to 10 weight percent, preferably of about 1 weight % to about 8 weight %.

Suitable hydrophilic monomers (i.e., monomers whose homopolymers are hydrophilic in accordance with this invention) include but are not limited to 2-hydroxyethylacrylate, 2-hydroxyethylmethacrylate, acrylamide, N-ornithine acrylamide, N-(2-hydroxypropyl)acrylamide, polyethyleneglycol acrylates, polyethyleneglycol methacrylates, N-vinyl pyrolidone, N-phenylacrylamide, dimethylaminopropyl methacrylamide, acrylic acid, benzylmethacrylamide, 4-hydroxybutylmethacrylate, glycerol mono methacrylate, glycerol mono acrylate, 2-sulfoethylmethacrylate, phenoxyethyl acrylate, phenoxy ethyl methacrylate, 2-(2-ethoxyethoxy)ethyl acrylate, 2-(2-ethoxyethoxy)ethyl methacrylate, furfuryl acrylate, furfuryl methacrylate, and methylthioethylacrylamide.

Suitable hydrophobic monomers (i.e., monomers whose homopolymers are hydrophobic in accordance with this invention) include but are not limited to Lauryl methacrylate, Lauryl acrylate, 2-ethylhexyl acrylate, 2-ethylhexyl methacrylate, n-decyl acrylate, n-decyl methacrylate, hexyl acrylate, hexyl methacrylate, stearyl acrylate, stearyl methacrylate, isodecyl acrylate, isodecyl methacrylate, isobornyl acrylate, isobornyl methacrylate, vinyl laurate, vinyl stearate, 1-hexadecyl acrylate, 1-hexadecyl methacrylate, n-myristyl acrylate, n-myristyl methacrylate, n-dodecyl methacrylamide, butyl acrylate, n-butyl methacrylate, isooctyl acrylate, isotridecyl acrylate, isooctyl methacrylate, and isotridecyl methacrylate.

Suitable crosslinkers include for example but are not limited to ethylene glycol dimethacrylate (EGDMDA), diethylene glycol dimethacrylate, triethylene glycol dimethacrylate and poly(ethylene glycol)dimethacrylate wherein ethylene glycol dimethacrylate is preferred. Suitable initiators include for example but are not limited to azobis (isobutyronitrile), 2,2'-azobis(2,4-dimethylvaleronitrile), 2,2'-azobis(methylbutyronitrile), 1,1'-azobis(cyanocyclohexane), di-t-butyl peroxide, dicumyl peroxide, t-butyl-cumyl peroxide, 2,5-dimethyl-2,5-bis(2-ethylhexanoyl peroxy)hexane, t-butyl peroxyneodecanote, t-butyl peroxy 2-ethylhexanoate, di(4-t-butyl cyclohexyl)peroxydicarbonate, t-butyl peroxypivalate, decanoyl peroxide, lauroyl peroxide, benzoyl peroxide, 2,4-pentanedione peroxide, di(n-propyl)peroxydicarbonate, t-amyl peroxyneodecanoate and t-butyl peroxyacetate wherein 2,2'-azobis(isobutyronitrile) is preferred. Suitable ultraviolet light absorbers include for example but are not limited to beta-(4-benzotriazoyl-3-hydroxyphenoxy)ethyl acrylate, 4-(2-acryloxyethoxy)-2-hydroxybenzophenone, 4-methacryloxy-2-hydroxybenzo-phenone, 2-(2'-methacryloxy-5'-methylphenyl)benzotriazole, 2-(2'-hydroxy-5'-methacryoxyethylphenyl)-2H-benzotriazole, 2-[3'-tert-Butyl-2'-hydroxy-5'-(3"-methacryloyloxypropyl]phenyl]-5-chloro-benzotriazole, 2-(3'-tert-Butyl-5'-[3"-dimethyl-vinyisilylpropoxy)-2'-hydro-xyphenyl]-5-methoxybenzotriazole, 2-(3'-Allyl-2'-hydroxy-5'-methylphenyl)benzotriazole, 2-[3'-tert-Butyl-2'-hydroxy-5'-(3"methacryloyloxypropoxy)phenyl]-5-methoxybenzotriazole, and 2-[3'-tert-Butyl-2'-hydroxy-5'-(3"-methacryloyloxy-propoxy)phenyl]-5-chlorobenzotriazole wherein beta-(4-benzotriazoyl-3-hydroxyphen-oxy)ethyl acrylate is the preferred ultraviolet light absorber.

A UV absorber optionally may be added to the copolymer compositions. A novel, preferred, UV/blue light absorber, i.e., vinyl anthracene, may be added to the copolymer compositions. Conventional UV absorbers such as a vinyl benzophenone or a vinyl benzotriazole also may be used.

TABLE 1

Examples 1-8:

| Example | Monomer | Concentration | RI | % EWC | Tg ° C. | ΔD upon hydration |
|---|---|---|---|---|---|---|
| 1 | PEA | 70 | 1.5341 | 7 | 2 | 0.6 |
|   | HEA | 27 |  |  |  |  |
|   | EGDM | 3 |  |  |  |  |
| 2 | PEMA | 67 | 1.5401 | 6 | 12 | 0.6 |
|   | HEA | 30 |  |  |  |  |
|   | EGDM | 3 |  |  |  |  |
| 3 | PEA | 67 | 1.5441 | 8 | 16 | 0.8 |
|   | HEMA | 30 |  |  |  |  |
|   | EGDM | 3 |  |  |  |  |
| 4 | BA | 70 | 1.5241 | 9 | 10 | 1.0 |
|   | HEA | 27 |  |  |  |  |
|   | EGDM | 3 |  |  |  |  |
| 5 | POEA | 70 | 1.5201 | 10 | 19 | 1.0 |
|   | HEMA | 27 |  |  |  |  |
|   | EGDM | 3 |  |  |  |  |
| 6 | BMA | 60 | 1.5312 | 8 | 18 | 0.8 |
|   | HEA | 20 |  |  |  |  |
|   | LM | 17 |  |  |  |  |
|   | EGDM | 3 |  |  |  |  |
| 7 | VC | 27 | 1.5213 | 6 | 10 | 0.5 |
|   | HEA | 20 |  |  |  |  |
|   | LM | 50 |  |  |  |  |
|   | EGDM | 3 |  |  |  |  |
| 8 | VC | 30 | 1.5422 | 14 | 7 | 0.8 |
|   | EHA | 42 |  |  |  |  |
|   | HEA | 25 |  |  |  |  |
|   | EGDM | 3 |  |  |  |  |

0.3% by weight of MEB was used in all copolymer compositions.
PEA: 2-phenylethyl acrylate
PEMA: 2-phenylethyl methacrylate
POEA: Phenoxyethyl acrylate
BA: Benzyl acrylate
BMA: Benzyl methacrylate
VC: vinyl carbazole
EHA: 2-ethylhexylacrylate
LM: Lauryl methacrylate
HEMA; Hyroxyethylmethacrylate
HEA: Hydroxyethylacrylate
EGDM: ethylene glycol dimethacrylates
MEB: 2-(2'-Methacryloxy-5'methylphenyl)benzotriazole General Preparation Steps for Polymers of Table 1, Example 1-8

The comonomers listed above were mixed in a glass flask using a magnetic stir bar for at least 30 minutes followed by sonication for the times indicated, and then stirring again for another 30 minutes.

We found that sonicating for about 30 minutes at a power setting of 100% on a Branson 5510 provides optically clear materials with adequate optical and physical properties. The monomer solution is degassed with argon and poured in 6 in.×6 in. molds made from glass plates separated by a silicone gasket. The molds were kept at 60° C. for 6 hours and then post-cured in vacuo at 100° C. for 12 hours.

The resulting copolymers are rigid enough to be machined at around room temperature. A unique aspect of the present invention is that the refractive index of these materials is so high that lenses are made thin enough to be folded without further processing or hydration.

IOLs are machined from the copolymers to exact diopters. The IOLs are hydrated in distilled water for 3 hours at 50° C. and the diopter measured again in a hydrated state. The value obtained is the actual power of the lens that should be used for labeling purposes.

Alternatively, a mathematical formula relating the diopter of a dry lens to that of the same lens hydrated may be developed from data such as that discussed below and used to label the IOLs.

Empirical Estimation of In-Vivo Lens Diopter

Unlike conventional hydrogel where lens hydration results into a significant decrease in diopter due to a decrease of RI of the polymer upon absorbing water, the lenses of the present invention exhibit a relatively modest change in diopter upon hydration due to the small amount of water absorbed and a counterbalancing effect of the lens swelling and concomitant steepening of the radius of curvature. Lenses were lathe cut from sheets made from polymer compositions made according to the procedure described previously. Ten (10) lenses were selected for each composition. Table 2 below shows the diopter of 20 D lenses made from polymer examples 1-8 before and after hydration:

TABLE 2

Examples 1-8:

| Example | RI | % EWC | Diopter before hydration (D) | SD* | Diopter after hydration (D) | SD |
|---|---|---|---|---|---|---|
| 1 | 1.5341 | 7  | 20.0 | 0.1 | 20.6 | 0.3 |
| 2 | 1.5401 | 6  | 20.0 | 0.2 | 20.6 | 0.3 |
| 3 | 1.5441 | 8  | 20.0 | 0.1 | 20.8 | 0.2 |
| 4 | 1.5241 | 9  | 20.0 | 0.1 | 21.0 | 0.2 |
| 5 | 1.5201 | 10 | 20.0 | 0.2 | 21.0 | 0.1 |
| 6 | 1.5312 | 8  | 20.0 | 0.2 | 20.8 | 0.3 |
| 7 | 1.5213 | 6  | 20.0 | 0.2 | 20.5 | 0.2 |
| 8 | 1.5422 | 14 | 20.0 | 0.2 | 20.8 | 0.3 |

*Standard deviation, of diopter measurement, n = 10.

What is claimed is:

1. A method of determining post-implantation diopter of a lens pre-implantation comprising the steps of:

(a) providing an intraocular lens (IOL) comprising a polymer for which the rigidity and refractive index is dependent upon its state of hydration, wherein the polymer comprises a first hydrophilic monomer and a second hydrophilic monomer selected from the group consisting of 2-phenylethyl acrylate, 2-phenylethyl methacrylate, hydroxyethylmethacrylate, and hydroxyethylacrylate, and further wherein one of the hydrophilic monomers is present in the polymer in an amount of about 70 weight percent;

(b) exposing the IOL of step (a) before implantation to a hydrating liquid for a length of time that the polymer of the IOL hydrates to a state of hydration which is substantially similar to the state of hydration the IOL polymer will obtain post-implantation;

(c) measuring the diopter value of the substantially hydrated IOL of step (b);

(d) partially dehydrating the substantially hydrated IOL of step (c) to enhance its handling characteristics and ease of implantation in an eye, wherein the partially dehydrated IOL after implantation in the eye will obtain the diopter value substantially that of the IOL measured pre-implantation.

2. A method according to claim 1 further comprising implanting the partially dehydrated IOL in an eye, wherein the implanting step is accomplished using an IOL injector means.

3. A method according to claim 1 wherein the IOL polymer has equilibrium water content in the range of about 3% to about 15% by weight.

4. A method according to claim 1 wherein the IOL polymer has equilibrium water content in the range of about 4% to 10% by weight.

5. A method according to claim 2 wherein the implanted IOL exhibits reduced or eliminated glistenings as experienced by the wearer, post-implantation.

6. A method according to claim 2 wherein the implanted IOL exhibits reduced or eliminated glistenings as experienced by the wearer, post-implantation.

7. A method according to claim 1 wherein the polymer further comprises a crosslinker.

8. The method of claim 7, wherein said polymer further includes an ultraviolet light absorbing material.

9. The method of claim 7, wherein said polymer includes an ultraviolet light absorbing material selected from the group consisting of beta-(4-benzotriazoyl-3-hydroxyphenoxy)ethyl acrylate, 4-(2-acryloxyethoxy)-2-hydroxybenzophenone, 4-methacryloxy-2-hydroxybenzo-phenone, 2-(2'-methacryloxy-5'-methylphenyl)benzotriazole, 2-(2'-hydroxy-5'-methacryoxy-ethylphenyl)-2H-benzotriazole, 2-[3''-tert-Butyl-2'hydroxy-5'-(3''-methacyloyloxypropyl)phenyl]-5-chlorobenzotriazole, 2-(3'-tert-Butyl-5'-(3-dimethylvinylsilypropoxy)-2'-hydroxyphenyl]-5-methoxybenzo-triazole, 2-(3'-Allyl-2'-hydroxy-5-'methylphenyl)benzotriazole, 2-[3'tert'-Butyl-2'-hydroxy-5'-(3''-methacryloyl-oxypropoxy)phenyl]-5-methoxybenzotriazole and 2-[3'-tert-Butyl-2'-hydr-oxy-5'-(3'''-methacryloyloxy-propoxy)phenyl]-5-chloro-benzotriazole.

10. The method of claim 8, wherein the ultraviolet light absorbing material is vinyl anthracene or derivatives therein.

* * * * *